US00PP13969P39

(12) United States Plant Patent
Davidson

(10) Patent No.: US PP13,969 P3
(45) Date of Patent: Jul. 15, 2003

(54) SHRUB ROSE PLANT NAMED 'MORDEN SUNRISE'

(75) Inventor: Campbell G. Davidson, Morden (CA)

(73) Assignee: Her Majesty the Queen in Right of Canada as represented by the Minister of Agriculture, Ottawa (CA)

( * ) Notice: Subject to any disclaimer, the term of this patent is extended or adjusted under 35 U.S.C. 154(b) by 149 days.

(21) Appl. No.: 09/826,366

(22) Filed: Apr. 5, 2001

(65) Prior Publication Data

US 2002/0199222 P1 Dec. 26, 2002

(51) Int. Cl.[7] ..... A01H 5/00
(52) U.S. Cl. ..... Plt./102

(58) Field of Search ..... Plt./102, 103, 104

*Primary Examiner*—Howard J. Locker
(74) *Attorney, Agent, or Firm*—Burns, Doane, Swecker & Mathis, LLP

(57) ABSTRACT

A new and distinct variety of shrub rose plant of relatively small stature is provided which forms in clusters attractive semi-double slightly concave yellow-orange blossoms that display a strong fragrance. The blossoming occurs substantially continuously over a long duration. An open and erect growth habit is exhibited. The foliage is glossy dark green and contrasts nicely with the yellow range blossoms. The plant propagates well by the use of softwood cuttings and possesses good winter hardiness. Good disease resistance particularly to blackspot is exhibited. It is particularly well suited for growing as an individual plant or as a mass planting to create ornamentation in the landscape.

3 Drawing Sheets

BOTANICAL/COMMERCIAL CLASSIFICATION

*Rosa hybrida*/Shrub Rose Plant

VARIETAL DENOMINATION cv. 'Morden Sunrise'

SUMMARY OF THE INVENTION

The new variety of *Rosa hybrida* of the present invention was created through a complex controlled breeding program using repeated crossings of shrub and garden roses at Morden, Manitoba, Canada. Hardiness was obtained from *Rosa arkansana* Porter, a species native to the Great Plains region of North America. The pollen parent in the final cross was the 'Sunsprite' variety (U.S. Plant Pat. No. 3,509) that displays deep yellow blossoms having approximately 28 petals. Other key antecedents include the 'White Bouquet' variety (U.S. Plant Pat. No. 1,415) that is a white-flowered Floribunda, the 'Hazeldean' variety (non-patented in the United States) a hybrid *Rosa spinosissia* that contributed both hardiness and yellow flower coloration, and the 'Assiniboine' variety (non-patented in the United States) which is the first of the PARKLAND series of roses and has been influential in developing roses that are well adapted to harsh prairie growing conditions.

It was found that a single plant of the new variety of Shrub rose plant was created through the breeding program. The new variety of the present invention displays the following combination of characteristics:

(a) commonly exhibits a relatively small stature combined with an erect and relatively open growth habit;

(b) forms in clusters on a substantially continuous basis attractive semi-double yellow-orange blossoms;

(c) forms attractive dark green glossy foliage;

(d) propagates well by the use of softwood cuttings;

(e) exhibits good winter hardiness;

(f) exhibits good disease resistance; and (g) is particularly well suited for growing as ornamentation in the landscape.

Rose plants of the new variety can be grown well on their own roots outdoors without protection at Morden, Manitoba, Canada. Blossom production commonly begins in early June at Morden, Manitoba, Canada and commonly is completed by mid-September. The attractive yellow-orange blossoms contrast nicely with the dark green glossy foliage.

Accordingly, the new variety well meets the needs of the horticultural industry. It can be grown to advantage as attractive ornamentation as an individual plant or as a mass planting in parks, gardens, public areas, and residential landscapes.

The characteristics of the new variety have been found to be homogenous and stable and have been shown to be strictly transmissible by asexual propagation by the rooting of softwood stem cuttings and by tissue culture conducted at Morden, Manitoba, Canada.

The new variety has been named 'Morden Sunrise'. The name was selected to reflect the attractive yellow-orange flower coloration and that reminds one of an early morning sunrise. It constitutes an attractive new member of the PARKLAND Series of roses.

BRIEF DESCRIPTION OF THE PHOTOGRAPHS AND DRAWING

The accompanying photographs show typical specimens of the new variety. The plants were photographed during the summer while growing outdoors on their own roots at Morden, Manitoba, Canada.

FIG. 1 illustrates a typical mature plant of the new variety. The relatively small plant stature with erect upright canes and a relatively open growth habit are shown.

FIG. 2 illustrates the typical semi-double yellow-orange blossoms in a cluster of two and the attractive dark green serrated glossy foliage of the new variety.

Figure 3:
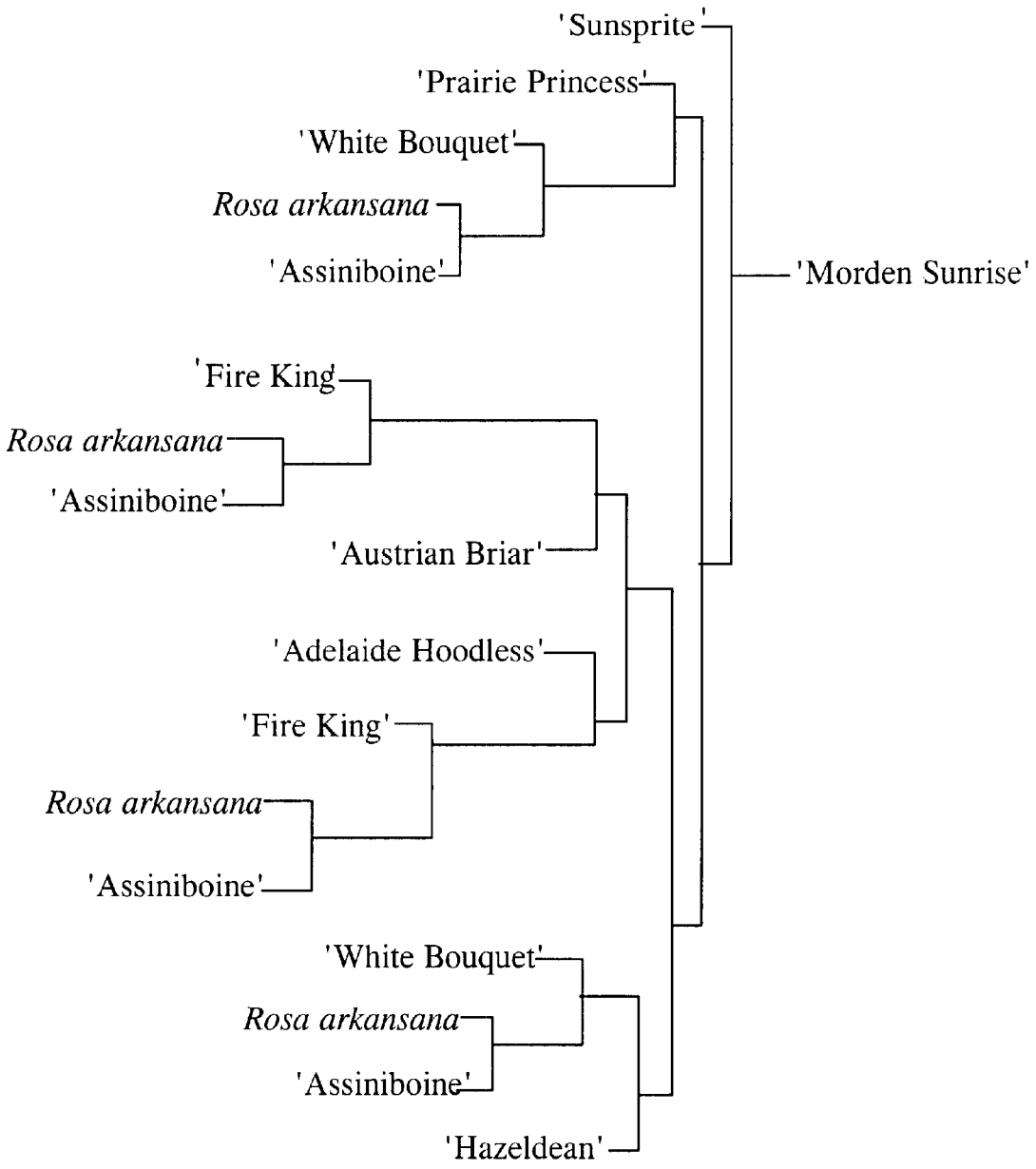

FIG. 3 provides the complex pedigree of the new variety wherein repeated crossings of shrub and garden roses where conducted.

DETAILED DESCRIPTION

The chart used in the identification of colors is that of The Royal Horticultural Society (R.H.S. Colour Chart). Common color terms are to be accorded their ordinary dictionary significance. The description is based on the observation of mature plants while growing on their own roots outdoors in the landscape during the summer at Morden, Manitoba, Canada.

Class: Shrub.

Plant:

*Height.*—Commonly approximately 62 to 83 cm with a mean height of approximately 70 cm. The height and width (reported hereafter) vary with environmental conditions. Greater measurements are encountered with warmer temperatures, greater precipitation and with fertilization (primarily nitrogen). Plants grown and overwintered in containers have reached over 1.5 m in height in the second year.

*Width.*—Commonly approximately 65 to 70 cm with a mean width of approximately 70 cm.

*Habit.*—Erect upright canes create a relatively open growth habit.

*Bark.*—Current season bark is Yellow-Green Group 144B and gradually darkens to Yellow-Green Group 146B on mature stems. In late fall to early winter the bark commonly continues to darken to Greyed-Purple Group 183B.

*Thorns.*—Mature stems typically bear a sparse to moderate quantity of prickles commonly having a length of approximately 5.4 to 9.2 mm and an average length of approximately 7.6 mm. On the current season's stems, smaller prickles commonly also are present in an infrequent quantity.

Leaves: Compound and odd pinnate.

*Leaflets.*—Number: commonly 3 to 7 with 5 leaflets being the most common. Configuration: oval tapering with a broad point. Margins: serrate (see FIG. 2). Size: terminal leaflets commonly range from approximately 4.6 to 5.6 cm in length (mean approximately 5.0 cm) and approximately 2.7 to 3.8 cm in width (mean approximately 3.2 cm). General appearance: dark green, and glossy. Petiolules: small and green and commonly approximately 2 to 2.2 mm in length. Color of young foliage: Yellow-Green Group 146B on the upper surface and Yellow-Green Group 146C on the under surface. Color of adult foliage: shiny dark green, Yellow-Green Group 147A on the upper surface and lighter duller green, Yellow-Green Group 148B on the under surface. Petioles: Green Group 138B, glandular, and with the sparse presence of prickles and a distinct groove.

Inflorescence:

*Number of flowers.*—Commonly in clusters of 2 to 15, and in clusters of 8 on average.

*Time of flowering.*—Blossoms begin to appear in mid- to late-June (mean week 26) and commonly continue through early September (mean week 37). Peak flower coverage based on percentage ratings over three years has been observed to be between early July (near week 27) and late August (mean week 34).

*Sepals.*—Commonly 2 to 3 cm. in length, Yellow-Green Group 147C on the outer surface and Yellow-Green Group 144B on the inner surface with a tomentose inner surface.

*Sepal extensions.*—Rarely present and average less than one of five randomly examined flowers.

*Buds.*—Shape: pointed. Color of newly opening buds: Upper surface: near Yellow Group 13A at the base, near Orange-Red Group 31B at the tip, and ranging from near Yellow Group 13A to Orange-Red Group 31B at the middle area. Under surface: near Yellow Group 13A at the base, near Orange-Red Group 32A at the tip, and ranging from near Yellow Group 13A to Orange-Red Group 32A at the middle area.

*Flower.*—Shape: slightly concave when fully open. The depth is approximately 2.5 cm when fully open. Diameter: commonly approximately 6 to 8 cm, and 7 cm on average. Color: generally yellow-orange as illustrated in FIG. 2 with the coloration changing (lightening) as the blossoms mature. When one-half open, the blossoms are dark orange with a yellow base. When three-fourths open, the blossoms are light orange with bright yellow. When fully open, the blossoms are yellow with near white. During the course of opening the inner petal coloration is Yellow Group 12A at the base, Yellow Group 11B at the middle and Red Group 37 C at the tip, and the outer petal coloration is Yellow Group 12A at the base, Yellow-Group 12C at the middle and Red Group 38C at the tip. Fragrance: strong. Petal number: semi-double, commonly approximately 12 on average. Petaloids: sometimes present and commonly in small numbers. When observing ten plants in three different age classes, the number of petaloids varied from 0 to 4 with a mean and standard error of 2.2+/−0.5. The number and size of the petaloids appears to be influenced by the environment and seasonal change. The coloration is Red Group 12A. Petal configuration: orbicular with a distinct point. The margins are smooth and slightly wavy. Petal drop: the petals drop cleanly and do not persist. Lasting quality: blossoms commonly last approximately seven days on average from the fully colored bud stage to petal drop. Filaments: commonly vary from bright yellow to orange in coloration. Anthers: commonly vary from deep yellow to orange in coloration and produce viable pollen. Pollen: yellow to yellow-orange in coloration and similar to the anthers in coloration. Style: medium in length and commonly extends slightly below the anthers. Receptacle: pear-shaped and round, Yellow-Green Group 144B in coloration, and generally less than 2 cm in diameter. Hips: substantially round in configuration, commonly display a mean size of approximately 12.9 mm×approximately 11.8 mm, and are formed each season but commonly do not ripen fully under the specified growing conditions. The hip coloration varies with stage of the ripening period from late August through October or hard frost. Initially the hips are near Yellow-Green Group 146B and change with increasing maturity to near Greyed-Orange Group 167A.

Development:

*Vegetation.*—Good vigor.

*Blossoming.*—The new variety is one of the earliest blooming of the PARKLAND Series of roses. Flower production commonly begins in early June on the previous season's wood and continues on current season's growth until approximately the middle of September. The mean flower duration is 15 weeks. The percent coverage of the blossoms compares favorably to that of other roses of PARKLAND Series of roses and with other yellow-flowered shrub roses under the specified growing conditions.

*Hardiness.*—Has survived in Agriculture Canada Hardiness Zone No. 3 with no protection. See Quellet and Sherk, *Can. J. Plant Sci.*, 47:3513–3518 (1967). Some stem dieback may occur in severe winters, but regrowth generally is very good if plants are propagated on their own roots.

*Resistance to diseases.*—Resistance has been good to local populations of blackspot (*Diplocarpon rosae* Wolf.), powdery mildew *Sphaerotheca pannosa* (Wallr. ex Fr.) Lev., and rust (*Phragmidium sp.*).

*Preferred mode of propagation.*—The use of softwood cuttings to produce self-rooted plants is recommended. For instance, softwood cuttings of 1 to 3 nodes in length can be taken during late spring through mid-summer, treated with rooting hormone (e.g. 3000 to 5000 mg/l indole-butyric acid) and placed under intermittent mist or fog to achieve high rates of propagation which commonly exceed 85 percent. Tissue culture also can be used for propagation. Budded or grafted roses may suffer winter injury at the specified growing location.

I claim:

1. A new and distinct variety of Shrub rose plant characterized by the following combination of characteristics:

(a) commonly exhibits a relatively small stature combined with an erect and relatively open growth habit, (b) forms in clusters on a substantially continuous basis attractive semi-double yellow-orange blossoms, (c) forms attractive dark green glossy foliage, (d) propagates well by the use of softwood cuttings, (e) exhibits good winter hardiness, (f) exhibits good disease resistance, and (g) is particularly well suited for growing as ornamentation in the landscape;

substantially as herein shown and described.

* * * * *